United States Patent [19]

Luebke et al.

[11] Patent Number: 5,210,327

[45] Date of Patent: May 11, 1993

[54] ETHERIFICATION WITH SKELETAL OLEFIN ISOMERIZATION

[75] Inventors: Charles P. Luebke, Mount Prospect; Bipin V. Vora, Darien; David A. Wegerer, Lisle; Joseph E. Zimmermann, Arlington Heights; Kevin C. Buck, Buffalo Grove, all of Ill.

[73] Assignee: UOP, Des Plaines, Ill.

[21] Appl. No.: 883,636

[22] Filed: May 15, 1992

[51] Int. Cl.⁵ .......................... C07C 41/06; C07C 5/22
[52] U.S. Cl. .................................... 568/697; 585/310; 585/314
[58] Field of Search ........................................ 568/697

[56] References Cited

U.S. PATENT DOCUMENTS

| | | | |
|---|---|---|---|
| 3,634,535 | 1/1972 | Haunschild | 260/7677 |
| 4,361,422 | 11/1982 | Derrien et al. | 568/697 |
| 4,513,153 | 4/1985 | Sandrin | 568/697 |
| 4,554,386 | 11/1985 | Groeneveld et al. | 568/697 |
| 4,581,474 | 4/1986 | Hutson, Jr. et al. | 568/697 |
| 4,778,943 | 10/1988 | Sun | 585/671 |
| 4,814,519 | 3/1989 | Harandi et al. | 568/697 |
| 4,950,803 | 8/1990 | Smith, Jr. et al. | 568/697 |
| 5,008,466 | 4/1991 | Schleppinghoff | 568/697 |

Primary Examiner—Howard T. Mars
Attorney, Agent, or Firm—Thomas K. McBride; John G. Tolomei

[57] ABSTRACT

A combination of an etherification process and a process for the isomerization of linear alkenes to isoalkenes uses a separation zone that receives an effluent stream from the etherification reaction zone and separates it into a high boiling stream, a low boiling stream and an intermediate boiling stream in order to reduce the mass flow of reactants through the isomerization and etherification reaction zones. The separation zone normally has an arrangement of a distillation column. The distillation column can provide a distillation function only, or can also provide a reactive distillation zone. The intermediate boiling stream typically leaves the column as a sidecut which in the case of reactive distillation is taken from the point above a bed of catalyst within the column. Taking the sidecut stream substantially eliminates the circulation of isoalkane hydrocarbons through the etherification and isomerization zone and maintains normal alkanes at an acceptable equilibrium level.

16 Claims, 1 Drawing Sheet

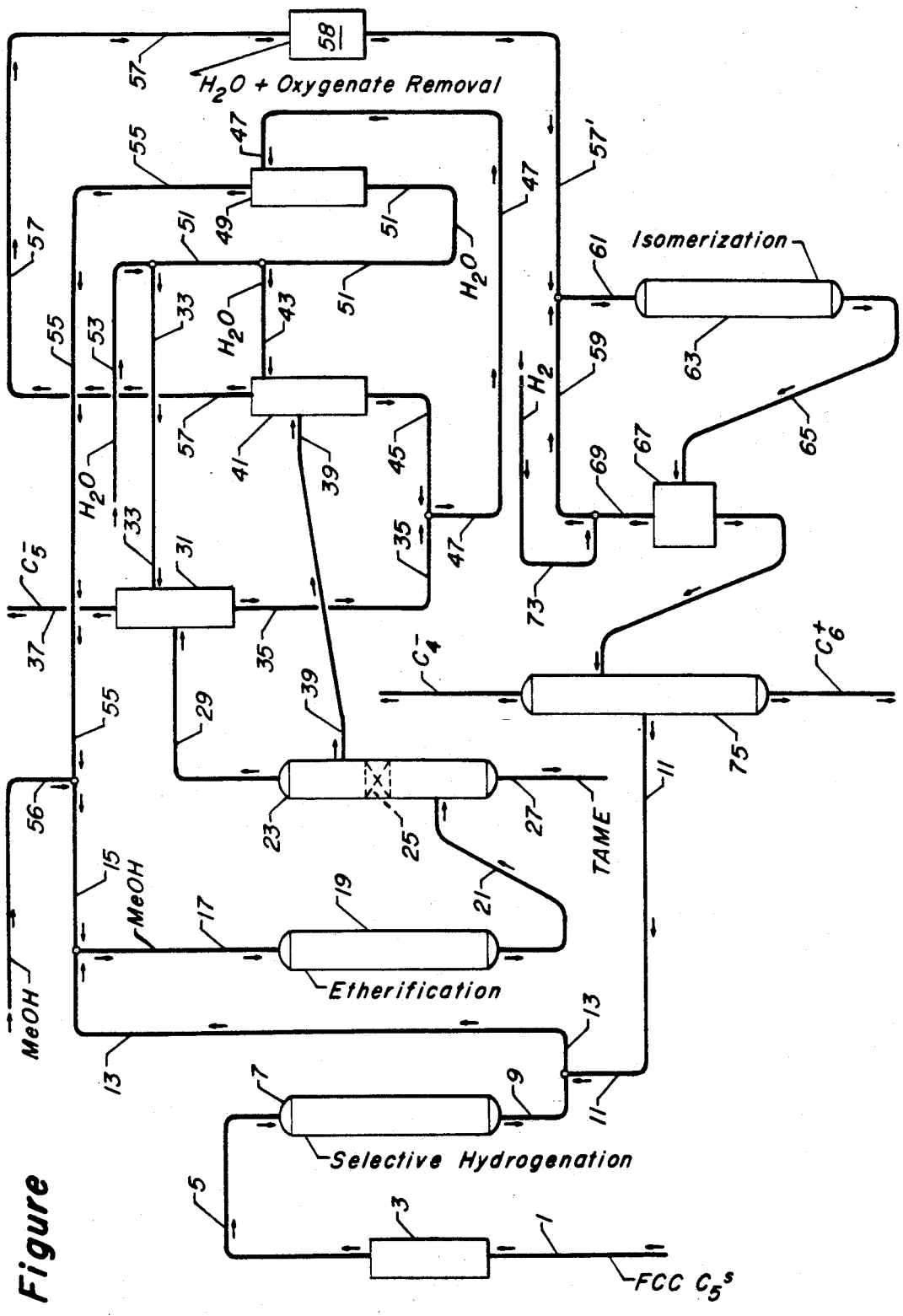

ETHERIFICATION WITH SKELETAL OLEFIN ISOMERIZATION

FIELD OF THE INVENTION

This invention relates to processes for the production of ethers by the reaction of an alcohol with an isoolefin. More specifically this invention relates to a process for the production of ether and the skeletal isomerization of olefins to provide additional feedstock for the production of ethers.

BACKGROUND OF THE INVENTION

The production of ethers by the reaction of an isoolefin and an alcohol are well known commercial operations. There are many detailed descriptions of processes for the production of such ethers, in particular, methyl tertiary butyl ether (MTBE) and methyl tertiary amyl ether (TAME). These ethers have long been known as useful octane blending agents for gasoline motor fuels due to their high octane number (RON) of about 120. More recently ether compounds as gasoline blending components have been highly valued as supplying oxygen to meet reformulated gasoline requirements. Processes for the production of MTBE and TAME by reacting methanol with isobutylene or isoamylene, respectfully, are among the most widely known processes for the production of such ethers.

Processes for the production of such ethers have suffered from a shortage of the necessary isoolefins for reaction with the alcohols to provide products. Feedstreams for etherification processes typically consist of a wide variety of olefinic and paraffinic isomers. It has been known to increase the available feedstock by the dehydrogenation of paraffins and the skeletal isomerization of olefins. Methods for the dehydrogenation of paraffins, in particular isoparaffins, are well known in the art as are processes for the skeletal isomerization of normal olefins to isoolefins. Since the olefinic and paraffinic isomers of any given carbon number have relatively close boiling points, separation of the isomers in an efficient manner to enhance the production of ether as well as the conversion of unreacted products to additional reactants have been difficult. Methods for the various separations have included adsorptive separations as well as extractive distillations. There is a need for etherification and isomerization process arrangements that simplify the separation of olefinic and paraffinic isomers to provide products and reactants.

SUMMARY OF THE INVENTION

This invention is a process that combines an etherification zone with a skeletal olefin isomerization zone in an arrangement that separates the higher boiling ether products from the lower boiling alcohols and isoparaffins while leaving an intermediate boiling stream that supplies linear alkenes to the skeletal olefin isomerization zone. The removal of the intermediate boiling stream concentrates a feedstream of linear alkenes to the reaction zone for the skeletal isomerization of the normal alkenes to isoalkenes. By taking the feedstream as an intermediate boiling cut, isoparaffins are rejected and linear alkenes are recycled while maintaining a low mass flow through the isomerization zone. Rejection of the isoparaffins from the feedstream eliminates the need for a drag stream of paraffins that was often required to prevent the build-up of such unreacted hydrocarbons in the recycle loop of the combined process. The overall smaller flowrate to the isomerization zone lowers the overall capital and operating cost of the unit while adding only additional minor cost to the distillation system for the combined process.

Accordingly in one embodiment, this invention is a process for the production of ether from a feedstream that includes normal alkenes, isoalkenes, normal alkane, and isoalkane isomers. The process comprises mixing an etherification input stream comprising isoalkenes, normal alkenes and normal alkanes with a $C_1$–$C_5$ monohydroxy alcohol to produce a combined feed and contacting the combined feed with an etherification catalyst in an etherification zone to react isoalkenes with the alcohol and produce an etherification effluent comprising ether and normal alkene and alkane isomers. A distillation zone input stream comprising at least a portion of the etherification effluent stream and including normal alkane, normal alkene and isoalkane isomers is passed to a distillation zone wherein it is separated such that a high boiling fraction comprising ether, a low boiling fraction comprising isoalkane, and an intermediate boiling fraction having an average boiling point between the low boiling and high boiling fraction is withdrawn. The intermediate boiling fraction comprises normal alkene and normal alkane isomers of the isoalkane that is withdrawn with the low boiling fraction. An isomerization zone feedstream, comprising at least a portion of the intermediate boiling stream, is passed to the isomerization reaction zone for the skeletal isomerization of normal alkenes and contacted with an isomerization zone catalyst. An isomerization zone effluent stream comprising isoalkenes is withdrawn from the isomerization zone and passed to the etherification reaction zone to provide at least a portion of the etherification reaction zone feedstream. A feedstream including normal alkene, isoalkene, normal alkane and isoalkane isomers is added to the process by passing it directly or indirectly into the etherification zone, the distillation zone and/or the isomerization zone.

Additional aspects of this invention relate to the arrangements required for distillation of feedstreams, reaction zone locations and treatment zones. In particular, another aspect of this invention is the reaction of unsaturated $C_4$ hydrocarbon isomers to produce MTBE and the reaction of unsaturated $C_5$ isomers for the production of methyl tertiary amyl ether. Another aspect of this invention is to withdraw the intermediate boiling stream as a sidecut from a distillation zone. The distillation zone may also provide reactive distillation to enhance the conversion of product and the recovery of potential reactants.

BRIEF DESCRIPTION OF THE DRAWING

The FIGURE shows a schematic illustration of a process of this invention showing the etherification zone, isomerization zone, distillation zone along with additional separators, and treating zones for the purification of the feedstream and product.

DETAILED DESCRIPTION OF THE INVENTION

This invention is broadly applicable to the production of a wide variety of ethers from a number of different feedstocks. The primary ethers for which this invention will be applied are tertiary, amyl and butyl ethers. The advantages of this invention are achieved when the feedstream includes a mixture of normal and branched alkene and alkane isomers. Where the etherification process is one for the production of butyl ethers, the typical feedstream will consist of a mixture of $C_4$ isomers comprising isobutane, isobutene, normal butane, 1-butene and 2-butene. Where the process is one for the production of amyl ethers, the feedstream components will include 3,methyl-1-butene, isopentane, 1-pentene, 2,methyl-1-butene, normal pentane, trans-2-pentene, cis-2-pentene and 2,methyl-2-butene in a typical distribution of isomers. Since in the combination of etherification and skeletal olefin isomerization processes, the alkanes are not reacted to any significant degree, these components increase the amount of material that passes through the process and must be removed to prevent an unacceptable build-up of unreacted products that circulate through the process. Although a variety of sources are available to provide such feedstreams, the most common source of the feedstreams for these processes are light cracked hydrocarbon streams from an FCC unit, or a $C_4$ stream from a steam cracker after butadiene extraction.

Often these hydrocarbon streams will contain diolefins in addition to the desired monoolefin feed components. These diolefins interfere with the operation of the catalyst in downstream processes by polymerizing and forming heavy hydrocarbon compounds that block the active sites of the catalyst and prevent their use. Preferably, feedstreams for this process will undergo treatment for the elimination of diolefins. A common method of eliminating diolefins is by the selective hydrogenation of the diolefins to saturate the diolefins into monoolefins while preserving monoolefins. Those skilled in the art know a variety of selective hydrogenation processes for the saturation of diolefins to monoolefins. A particular catalyst and operating conditions for such selective hydrogenation processes can be found in U.S. Pat. Nos. 4,695,560 and 4,734,540 the contents of which are hereby incorporated by reference. The selective hydrogenation process typically employs a nickel on aluminum catalyst or a noble metal, such as palladium on alumina, for the selective hydrogenation. The nickel may be sulfided or unsulfided. The process can also operate at a broad range of operating conditions including pressures of from 40 to 800 psig with pressures of between 50 and 300 psig being preferred and temperatures of from 70°–700° F. with temperatures of from about 120°–400° F. being preferred. Effective space velocities for the processes should be above 1 $hr^{-1}$ and preferably are above 5 with a range of from between 5 to 35 $hrs^{-1}$. It is typical in such processes to limit the amount of hydrogen to prevent the saturation of monoolefins such that there is less than 2 times the stoichiometric amount of hydrogen required for the selective hydrogenation in the process. Preferably, the mol ratio of hydrogen to diolefinic hydrocarbons in the material will be in a range of from 1:1 to 1.8:1, and in some cases the hydrogen will be less than stoichiometrically required amount of hydrogen. Additional information related to the selective hydrogenation of diolefinic hydrocarbons, and in particular, unconjugated diolefinic hydrocarbons, can be found in U.S. Pat. No. 4,695,560.

The feed to the process includes an alcohol to react with the isoolefin and produce the desired ether product. The alcohols that can be used are typically $C_1$–$C_5$ monohydroxy alcohols. Methanol typically constitutes the alcohol of choice for the etherification process. Ethanol, although used less commonly, is also a commonly available alcohol for the etherification process. Methanol is preferred somewhat since it is a stable commercial chemical of long standing.

The isoalkene as well as the normal alkene hydrocarbons will enter the etherification zone along with the alcohol. Contact with the etherification catalyst at etherification conditions will produce the ether product. A wide range of materials are known to be effective as etherification catalysts for the isoalkene reactants including mineral acids such as sulfuric acid, boron trifluoride, phosphoric acid on kieselguhr, phosphorus-modified zeolites, heteropoly acids, and various sulfonated resins. The use of a sulfonated solid resin catalyst is preferred. These resin type catalysts include the reaction products of phenolformaldehyde resins and sulfuric acid and sulfonated polystyrene resins including those crosslinked with divinylbenzene. A particularly preferred etherification catalyst is a macroporous acid form sulfonic ion exchange resin such as a sulfonated styrene-divinylbenzene resin as described in U.S. Pat. No. 2,922,822 having a degree of crosslinking of from about 5 to 60%. Suitable resins are available commercially. Specialized resins have been described in the art and include copolymers of sulfonyl fluorovinyl ether and fluorocarbons as described in U.S. Pat. No. 3,849,243. Another specially prepared resin consists of the $SiO_2$-modified cation exchangers described in U.S. Pat. No. 4,751,343. The macroporous structure of a suitable resin is described in detail in U.S. Pat. No. 5,012,031 as having a surface area of at least 400 $m^2$/g, a pore volume of 0.6–2.5 ml/g and a mean pore diameter of 40–1000 angstroms. It is contemplated that the subject process could be performed using a metal-containing resin which contains one or more metals from sub-groups VI, VII or VIII of the Periodic Table such as chromium, tungsten, palladium, nickel, chromium, platinum, or iron as described in U.S. Pat. No. 4,330,679. Further information on suitable etherification catalysts may be obtained by reference to U.S. Pat. Nos. 2,480,940, 2,922,822, and 4,270,929 and the previously cited etherification references.

A wide range of operating conditions are employed in processes for producing ethers from olefins and alcohols. Many of these include vapor, or mixed phase operations. Processes operating with vapor or mixed phase conditions may be suitably employed in this invention. The preferred etherification process uses liquid phase conditions.

The range of etherification conditions for processes operating in liquid phase still includes a broad range of suitable conditions including a superatmospheric pressure sufficient to maintain the reactants as a liquid phase, generally below about 700 psig, and a temperature between about 85° and about 210° F. Even in the presence of additional light materials, pressures in the range of 140 to 580 psig are sufficient. A preferred temperature range is from 100°–210° F. The reaction rate is normally faster at higher temperatures but conversion is more complete at lower temperatures due to favorable thermodynamic equilibrium. High conversion in a moderate volume reaction zone can, therefore, be obtained if the initial section of the reaction zone, e.g., the first two-thirds, is maintained above 160° F. and the remainder of the reaction zone is maintained below 120° F. This may be accomplished most easily with two reactors. The ratio of feed alcohol to isoolefin should normally be maintained in the broad range of 1:1 to 2:1. With the isobutene and isopentene reactants, good results are achieved if the ratio of methanol to isobutene is between 1.05:1 and 1.5:1. An excess of methanol, above that required to achieve satisfactory conversion at good selectivity, should be avoided as some decomposition of methanol to dimethyl ether may occur which may increase the load on separation facilities. Various etherification process techniques, reaction conditions and product recovery methods are described in U.S. Pat. Nos. 4,219,678 to Obenaus et al. and 4,282,389 to Droste et al. which are incorporated herein for this teaching.

The etherification zone operates selectively to principally convert only the isoolefins. Therefore, alkanes and normal alkenes pass through the etherification zone without any significant conversion to products or by-products. Thus, the etherification zone effluent together with the unreacted feed components provides a stream of ether product and normal and branched alkenes and alkane isomers for separation. In most cases, the stream entering the separation zone will also contain unreacted alcohol. The separation zone receiving the ether products, alcohol and unreacted alcohol distills the product into three separate boiling point fractions. Similar to most separation systems for recovery of ethers, the product separation zone provides a high boiling fraction that principally contains ether product. The product separation zone of this invention separates the remaining lower boiling components into a low boiling fraction containing isoalkane and lower boiling components and an intermediate boiling fraction that contains normal alkenes and alkanes that were not reacted in the etherification process or enter the separation zone directly as part of the process feed. Isoparaffins typically provide the lowest boiling constituent of the alkene and alkane isomers. The isoalkane isomers are conveniently withdrawn with the low boiling fraction from the separation zone.

In a continuously circulating process of this invention, the normal alkanes must also find a path out of the process loop in order to prevent their build-up. Typically, this process arrangement will withdraw a portion of the normal alkanes with the low boiling fraction from the separation zone. Withdrawal of the normal alkanes with the low boiling fraction establishes an equilibrium concentration of normal alkanes that controls their build-up in the recycle loop of the invention. The cut point for the intermediate boiling stream is set to maximize the removal of the isoalkane hydrocarbons and minimize the loss of normal alkenes between the low boiling fraction and the intermediate fraction. The arrangement of the separation zone typically consists of a single distillation column with the low boiling point fraction taken as an overhead, the high boiling point fraction taken as a bottoms stream, and the intermediate boiling point fraction taken as a sidecut from the column. Removal of the sidecut stream presents little problem for a typical etherification arrangement that already uses a distillation column. The sidecut of the normal alkene rich stream is taken a few trays below the overhead and will normally require the addition of only a few trays to the distillation column. It has been found that only a minimal amount of the normal alkene hydrocarbons are lost with the overhead by the method of this invention while still maintaining the equilibrium of normal alkanes circulating through the process at a reasonable level. The cut point between the high boiling fraction and the intermediate fraction is readily determined on the basis of maximizing the ether recovery. The separation between the low boiling fraction and the intermediate fraction is usually not critical when the ether is used for fuel blending purposes since the normal alkene and alkane hydrocarbons present in the intermediate stream are usually suitable gasoline components.

The separation zone of this invention is best suited to the production of a single ether product. For example, in the case of MTBE or TAME, the invention extracts one group of normal alkanes as the isomers for withdrawal from the separation zone as the intermediate boiling product. In the case of a typical MTBE process, the high boiling fraction will comprise MTBE, the low boiling fraction will include methanol and isobutane, and the composition of the intermediate fraction includes primarily normal butane, 1-butene and 2-butene. Sidecut withdrawal is set to minimize the loss of 1-butene with the overhead while taking out sufficient normal butane with the overhead to maintain a reasonable level of normal butane in circulation through the process. Where the process is used for the production of TAME, the high boiling stream comprises the ether product, isopentane and lesser amounts of normal pentane comprise major components of the low boiling stream, and the intermediate boiling fraction contains the normal pentene and some isopentene isomers along with a substantial quantity of normal pentane that is maintained at a desired concentration level through the circulating $C_5$ hydrocarbons. In the pentene operation, the separation point between the low boiling and high boiling streams again seeks to maximize isopentane recovery while minimizing the loss of normal pentenes.

A useful arrangement for the separation zone of this invention is the use of a reactive distillation zone that contains a bed of etherification catalyst. The distillation zone can provide additional etherification of unreacted isoalkanes, and thus minimize their concentration in the intermediate boiling sidecut stream. Therefore, the reactive distillation zone can be used as a combined reactor and separation zone with the removal of the intermediate boiling fraction from the combined reaction and distillation zone. Processes for the production of ether by catalytic distillation are well known to those skilled in the art and are taught in U.S. Pat. Nos. 3,634,535 and 4,950,803. Where the distillation zone is a catalytic distillation zone, the preferred arrangement introduces the feed to a point below a bed of catalyst within the distillation zone. The high boiling fraction is withdrawn from the higher boiling point region below the bed of catalyst while the intermediate boiling stream typically has a withdrawal point in the relatively lower boiling region above the bed of catalyst. Catalytic distillation for the production of ethers typically employs the same operating conditions as those generally taught for etherification. No particular apparatus or arrangement is needed to retain the catalyst bed within the distillation zone and a variety of methods can be used to incorporate the bed or region of catalyst within the distillation zone. For example, catalyst may be retained between suitable packing materials or may be incorporated on to a distillation tray itself. A preferred method of retaining the catalyst is through the use of corrugated structural devices and is described in U.S. Pat. No. 5,073,236 which is hereby incorporated by reference.

In most cases, the process arrangement will also include methods for recovering the unreacted alcohol. Those skilled in the art are familiar with the various azeotropes formed by the ether products and alcohol and can provide suitable means for such separations and recoveries. As anticipated for most cases, methanol will be the usual alcohol and both the low boiling point fraction and the intermediate fraction will ordinarily undergo an alcohol recovery step. Water washing provides the usual means for recovering methanol in such arrangements.

Following etherification and separation, the intermediate boiling fraction undergoes skeletal isomerization of the normal alkenes to produce additional isoalkenes for the etherification process. In order to maintain catalyst stability in the isomerization zone, the streams contacting the catalyst may require removal of polar contaminants such as sulfur, nitrogen or oxygen compounds. Thus, in addition to processing for the recovery of methanol, the intermediate boiling fraction may also require additional purification for the removal of compounds that can poison the catalyst or interfere with the skeletal isomerization process. Compounds that are usually most harmful to the isomerization catalyst include water, oxygenate compounds and nitrogen compounds. The water and oxygenate compounds suppress the isomerization catalyst activity. The nitrogen compounds also affect the isomerization catalyst activity and results in a reduced activity. These nitrogen compounds are also poison to acidic ion exchange resins used for the etherification and thus are also beneficially removed prior to the etherification. A variety of methods are known to remove such compounds which include water washing, adsorption and extraction processes. Oxygenate compounds and nitrogen compounds can be removed by typical adsorbents for the removal of these contaminants comprised zeolitic molecular sieves. Suitable types of zeolites are faujasites having pore sizes of about 10 angstroms. In particular, such zeolites include X, Y and L types as described in U.S. Pat. Nos. 3,216,789; 2,882,244 and 3,130,007. A particularly preferred type of zeolite is 13X. The use of type 13X sieves for the removal of oxygenate compounds such dimethyl ethers from the effluent from an etherification process is described in U.S. Pat. No. 4,814,517, the contents of which are hereby incorporated by reference. Suitable operation of the isomerization zone will require the removal of water and oxygenate compounds to a level of less than 50 wppm, and preferably less than 5 wppm water equivalents. Common nitrogen and oxygenate compounds that have also been found in light cracked products from an FCC unit include acetone and acetonitrile. These compounds are preferably removed by water washing such feeds prior to introduction into the process.

The normal alkene-rich input stream after purification enters the isomerization zone. Methods for converting the normal alkene components to isoalkene components by isomerization are well known in the art. A process for converting linear alkenes to isomerized alkenes using a crystalline or silicate molecular sieve is taught in U.S. Pat. No. 4,503,282. Additional catalyst and methods for the skeletal isomerization of linear alkenes are described in U.S. Pat. Nos. 4,778,943 and 4,814,519. A preferred catalyst for the isomerization reaction zone of this invention is a non-zeolitic molecular sieve. Preferred forms of the non-zeolitic molecular sieve for this invention includes silicoaluminophosphates and a magnesium aluminophosphate. Suitable non-zeolitic catalysts such as the SAPO and MgGAPO are described in U.S. Pat. Nos. 4,440,871 and 4,758,419 which are hereby incorporated by reference. The catalyst for the isomerization zone typically lies in a fixed bed arrangement. In order to permit in-situ regeneration, the isomerization zone may include multiple reactors in a swing bed arrangement. Preferably, the reactants contact the catalyst in a vapor phase flow. Contacting a linear alkene feed with a catalyst in the presence of hydrogen in a molar ratio of from about 0.01 to 9, and preferably in a ratio of from 1 to 7, aids the process by suppressing the formation of carbon compounds on the catalyst. The isomerization process will typically operate over a broad range of conditions including temperatures of from 120°–1300° F. with temperatures in the range of 200°–1000° F. being preferred. Pressures for the isomerization reaction will also vary over a wide range extending from atmospheric conditions to 700 psig, and preferably are in a range of 50 to 350 psig. Space velocities can also vary over a wide range from 0.5 to 100 hr$^{-1}$ with a preferred range of 1–5 hr$^{-1}$. The expected per pass conversion of normal alkenes to isoalkenes in the isomerization zone will generally reach at least 40% of the total combined feed entering the reaction zone and will more typically exceed 50%.

The effluent stream from the isomerization zone containing isoalkenes normally undergoes separation for the recovery of light gases including hydrogen. Hydrogen recovered in the light gases from the isomerization zone is recycled to the inlet of the isomerization zone to provide any necessary hydrogen concentration. The effluent from the isomerization zone may also undergo additional separation to remove additional light ends or reject heavier by-product hydrocarbons. The presence of light ends in the isomerization zone effluent passes this light material on to the etherification zone as uncondensibles that, when rejected from the etherification separation system, drag methanol into downstream facilities thereby causing corrosion problems and methanol loss. Heavy materials such as $C_6^+$ hydrocarbons tend to foul or deactivate the etherification catalyst.

In the simplest arrangement of this invention, the effluent from the isomerization zone, after any separation, is admixed with the feed to the etherification zone to provide additional isoalkene reactants. The return of the isomerization effluent to the etherification reaction provides a loop incorporating components that are recycled through the process. Preferably, the feedstream of mixed, branched, and normal alkenes and alkanes will enter the process at a point in the loop just ahead of the etherification reaction zone. However, this feedstream may be added at a number of different points, depending on its composition, within this loop. For example, it is also possible to add the feedstream at a point just ahead of the distillation column. In this way the total flow of reactants through the etherification zone is reduced by eliminating nonreactive isoalkane hydrocarbons. Those skilled in the art are aware of the particular characteristics of the feedstream and the desired product streams that will dictate the most advantageous location for introducing the feedstream.

EXAMPLE 1

This invention is further described in the context of an example for the production of methyl tertiary amyl ether using a process or an arrangement as shown in FIG. 1. This example presents engineering calculations based on data from operating process units and laboratory test results. Relative flowing compositions for the major process streams of this Example are shown in Table 1 on a water-free basis. In this example, a feed comprising a $C_5$ cut from the product stream of a fluidized catalytic cracking unit enters the process through line 1 and passes through a water wash zone 3. Water wash zone 3 removes soluble nitrogen compounds and light oxygenates from the feed. Line 5 recovers the purified feed at a liquid flow of 7620 barrels per day and passes the feed to a selective hydrogenation reactor 7 for the removal trace diolefin compounds. Line 9 carries the treated FCC feed which is saturated with water to a level of about 400 wppm and on a water-free basis has the relative flowing composition given in Table 1. Line 9 admixes the treated FCC feed with 7459 barrels per day of recycle stream carried by line 11 and having a relative composition given in Table 1. Methanol in an amount of 748 lb-mol/hr carried by line 15 mixes with the combined C5 feed carried by line 13 to provide an etherification feedstream passed by line 17 into an etherification reactor 19. Etherification reactor 19 contacts the combined feed with a sulfonated solid resin catalyst at a temperature of about 170° and a pressure of about 88 psig. Catalyst in etherification reactor 19 is arranged as a solid bed. A line 21 carries the effluent from etherification reactor 19 to a distillation column 23 having a second bed of sulfonated solid resin catalyst 25 located in an upper portion of the distillation column. Table 1 lists the relative composition of line 21. The contents of line 21 enters column 23 at an average temperature of about 170° F. and a pressure of 88 psig. A bottoms stream 27 carries the tertiary methyl amyl ether product from the column and has the relative composition given in Table 1. An overhead stream 29 carries unreacted methanol and isopentane and lighter hydrocarbons from column 23. A portion of the overhead carried by line 29 is cooled, condensed and refluxed to the top of column 23 after separation of light gases in a condensing section (not shown). Line 29 carries the remainder of the effluent to a water wash column 31. Recycled and fresh water, entering column 31 from a line 33, carries methanol downward through the column where a line 35 takes the methanol along with the water. A C5 drag stream in the form of the overhead line 37 leaves the top of water wash zone 31 and has the relative composition given in Table 1. Column 23 also provides a sidecut stream which is taken from a location above bed 25 by line 39. Line 39 transfers the sidecut stream to a water wash column 41 for the removal of methanol and other oxygenate streams from the sidecut. A line 43 charges water to the top of water wash column 41 which is collected by a line 45 and combined with the methanol and water from water wash column 31 into a stream 47. The contents of stream 47 enter a methanol separation column 49 for the recovery of water from the methanol stream. Water recovered from column 49 passes through a line 51 to supply water for column 41 through line 43 and is combined with make-up water from a line 53 to provide the water stream 33 for column 31. A line 55 carries methanol from the top of column 49 and combines it with fresh methanol entering by a line 56 to provide the methanol for the etherification through line 15. Water washed hydrocarbons from methanol recovery column 41 pass overhead via line 57 and through a water and oxygenate removal zone 58 for the withdrawal of trace amounts of oxygenates such as dimethyl ether and water. Treatment of stream 57 in removal zone 58 lowers the concentration of water and water equivalent in line 57 to less than 30 wppm and yields a stream having the composition given in Table 1. The contents of line 57' are combined with a hydrogen recycle stream which is carried by line 59 to form a combined feed 61 that enters a reactor 63 for the skeletal isomerization of normal pentenes to isopentenes. Table 1 lists the composition of the hydrogen recycle stream carried by line 59. The combined feed enters the isomerization reaction zone at a temperature of about 120° F. and a pressure of about 290 psia. The combined feed contacts a silicoaluminophosphate catalyst of the SAPO-11 type within the reaction zone. Line 65 withdraws the product effluent from the isomerization reactor which passes through a liquid vapor separation zone 67. The liquid vapor separation zone recovers a hydrogen rich stream 69 which mixes with additional make-up hydrogen from line 73 to provide the hydrogen recycle stream 59. A line 71 transfers the heavier components from separator 67 to a distillation column 75. Column 75 fractionates light ends comprising $C_4^-$ materials overhead through a line 77 and drops $C_6^+$ components out of the process through a line 79. Line 11, having the composition previously described, in a table carries the isopentane rich stream from column 75 for combination with the FCC feed.

TABLE 1

| | STREAM COMPOSITION - MOL % | | | | | | |
|---|---|---|---|---|---|---|---|
| | Line 9 | Line 11 | Line 21 | Line 27 | Line 37 | Line 57 | Line 59 |
| $H_2$ | — | 1.39 | .57 | — | .04 | — | 91.51 |
| $C_1$-$C_4$ | 5.44 | 1.35 | 2.67 | .19 | 9.58 | .87 | .35 |
| 3M-1-butene | 1.68 | .55 | .88 | — | 2.25 | 1.03 | .06 |
| isopentane | 35.70 | 56.81 | 37.14 | .11 | 67.78 | 57.66 | 5.11 |
| 1-Pentene | 4.98 | .87 | 2.30 | .03 | 3.30 | 4.03 | .07 |
| 2M-1-Butene | 9.60 | 4.41 | .55 | .01 | .19 | .25 | .33 |
| Normal Pentane | 6.18 | 14.01 | 8.13 | 3.47 | 8.91 | 14.14 | 1.34 |
| Trans-2-Pentene | 9.23 | 4.07 | 5.27 | 1.68 | 3.93 | 10.38 | .26 |
| Cis-2-Pentene | 7.48 | 3.50 | 4.36 | 1.80 | 2.99 | 8.52 | .22 |
| 2M-2-Butene | 16.99 | 12.45 | 5.50 | .27 | 1.00 | 2.90 | .74 |
| $C_5$ Cyclic | 1.15 | .21 | .53 | 2.42 | .02 | .22 | |
| $C_6^+$ | 1.56 | .38 | .77 | 3.99 | | | |
| $H_2O$ wppm | 400 | 400 | 400 | 400 | 400 | 400 | 400 |
| Methanol | — | — | 20.08 | | | | |
| TAME | — | — | 11.23 | 86.03 | | | |

EXAMPLE 2

This example presents engineering calculations for a process arrangement for the production of MTBE in combination with a butene isomerization zone wherein the effluent from the etherification zone enters a butene distillation column. Two cases are studied in the Example to compare the operation of the process in a case where the distillation zone provides a sidecut of feed to the isomerization zone to a case where the distillation zone operates without the sidecut. Both arrangements process a feedstream of 5400 barrels per day of $C_4$ material from an FCC unit. The process arrangement is similar to that described in the FIGURE except for the arrangement of the distillation zone. The arrangement of this example uses a simple distillation zone without reactive distillation. The mixed $C_4$ feed is combined with a methanol stream and passed through an MTBE reactor containing a bed of sulfonated solid resin catalyst. In the case without the sidecut, the MTBE effluent passes to a distillation zone arranged to provide an overhead stream which after removal of light material will provide a feedstream to an isomerization reactor for the skeletal isomerization of olefins and a bottoms stream providing an MTBE product. After treatment for removal of light ends and methanol, the overhead from the distillation column has the composition given in Table 2. The distillation column overhead passes to the isomerization reaction zone where it contacts a silicoaluminophosphate type catalyst and converts the linear butenes to isobutene. The effluent from the isomerization reaction zone passes to a separator for the recovery of a hydrogen recycle stream which is admixed with the distillation column overhead providing the feed to the isomerization reaction zone. The remainder of the effluent from the isomerization reaction zone is passed in combination with the feed to the MTBE unit. In an operation without the sidecut, the isomerization zone receives a total feed of 27,600 barrels per day at the butene conversions as shown in Table 2.

A second case of the butene isomerization/MTBE process of this Example, arranged in accordance with this invention, withdraws a sidecut stream from the distillation zone in addition to the overhead liquid. The composition of the additional sidecut stream taken in accordance with the arrangement of this invention is shown in Table 2. The sidecut obtained by the arrangement of this invention passes to an isomerization reaction zone operated in essentially the same manner as that described for the distillation arrangement without the sidecut stream. By the addition of the sidecut stream, the total feed to the isomerization reaction zone is reduced to 15,580 barrels per stream day.

A comparison of the two arrangements as shown in Table 2 demonstrate the advantages of this invention. In both arrangements with and without the sidecut, the total normal butene conversion was 73 mol % with a total butene conversion of 80%. However, with the addition of the sidecut, the feed to the isomerization reaction zone was substantially reduced from 27,600 barrels per stream day to 15,580 barrels per stream day. The addition of the sidecut permits the withdrawal of the isobutane rich overhead stream from the distillation column and the removal of the isobutane rich stream from the process. In addition to reducing the total mass flow through the isomerization reactor, the elimination of the overhead components from the process with the sidecut arrangement also reduces the combined feed to the MTBE unit. Accordingly, the combined feed to the MTBE unit decreases from 6.1 to 3.9 with the addition of the sidecut. Thus, the addition of the sidecut as studied in Example 2 establishes that a significant savings in reactor size can be obtained in both the MTBE and isomerization reaction zones.

TABLE 2

| BUTENE ISOMERIZATION/MTBE | | |
|---|---|---|
| | Distillation Column With Overhead to Isom | Distillation Column With Sidecut to Isom |
| Fresh feed, BPSD | 5407 | 5407 |
| Combined feed to MTBE, BPSD | 33,076 | 21,056 |
| Combined feed ratio at MTBE | 6.1 | 3.9 |
| Butene Column Overhead liquid composition, mol % | | |
| isobutane | 56.34 | 55.11 |
| isobutylene | 0.005 | 0.008 |
| 1-butene | 2.33 | 3.90 |
| n-butane | 18.00 | 17.58 |
| 2-butene | 18.61 | 17.63 |
| Other | 4.76 | 5.77 |
| Sidecut composition, mol % | | |
| isobutane | — | 14.70 |
| isobutylene | — | 0.01 |
| 1-butene | — | 3.88 |
| n-butane | — | 34.55 |
| 2-butene | — | 42.92 |
| Feed to Isom. BPSD | 27,600 | 15,580 |
| Butene conversion, mol % | | |
| n-butenes | 73 | 73 |
| total butenes | 80 | 80 |

What is claimed is:
1. A process for the production of ether from a feedstream including normal alkene, isoalkene, normal alkane and isoalkane isomers, said process comprising:
 (a) mixing an etherification input stream comprising isoalkenes, normal alkenes and normal alkanes with a $C_1$-$C_5$ monohydroxy alcohol to produce a combined feed and contacting said combined feed with an etherification catalyst in an etherification zone at etherification conditions to react isoalkenes with said alcohol and produce an etherification effluent stream comprising ether and normal alkane and normal alkene isomers;
 (b) passing a distillation input stream comprising at least a portion of said etherification effluent stream and including normal alkane, normal alkene and isoalkane isomers to a distillation zone, separating said distillation input stream and withdrawing from said distillation zone a high boiling fraction comprising said ether, a low boiling fraction comprising said isoalkane, and an intermediate boiling fraction having an average boiling point between said low boiling and said high boiling fraction said intermediate fraction comprising normal alkene and normal alkane isomers of said isoalkane;
 (c) passing an isomerization zone feedstream comprising at least a portion of said intermediate boiling stream to an isomerization reaction zone for the skeletal isomerization of normal alkenes and contacting said intermediate boiling stream with an isomerization catalyst at isomerization conditions;
 (d) withdrawing an isomerization zone effluent stream comprising isoalkenes from said isomerization zone and passing at least a portion of said isomerization zone effluent to said etherification reaction zone to provide at least a portion of said etherification reaction zone feedstream; and,
 (e) passing said feedstream including normal alkene, isoalkene, normal alkane and isoalkane isomers into at least one of said etherification zone, said distillation zone and said isomerization zone.

2. The process of claim 1 wherein said feedstream is first passed into said etherification zone.

3. The process of claim 1 wherein said isomers comprise $C_4$ or $C_5$ hydrocarbons and said alcohol comprises methanol or ethanol.

4. The process of claim 1 wherein said distillation zone contains a bed of etherification catalyst to produce ether, unreacted normal alkene and normal alkane isomers pass upwardly through said bed and said intermediate boiling stream comprises normal alkene and normal alkane isomers that have passed through said bed.

5. The process of claim 1 wherein said low boiling stream contains a greater amount of said isoalkane isomer than said intermediate stream.

6. A process for the production of tertiary amyl ether from a feedstream including normal pentane, isopentane, normal pentene, and isopentene, said process comprising:
   (a) mixing said feedstream and an isomerization zone effluent stream with a $C_1$–$C_5$ monohydroxy alcohol to produce a combined feed and contacting said combined feed with an etherification catalyst in an etherification zone at etherification conditions to react isopentenes with said alcohol and produce an intermediate etherification effluent stream comprising tertiary amyl ether, unreacted alcohol, normal pentane, normal pentene, isopentene and isopentane;
   (b) passing said intermediate etherification effluent to a reactive distillation zone containing a bed of etherification catalyst and contacting said etherification zone effluent and said alcohol in said bed of catalyst at etherification conditions, withdrawing from said distillation zone at a location below said bed of catalyst a high boiling fraction comprising said tertiary amyl ether, and withdrawing from said distillation zone at a location above said bed of catalyst, a low boiling fraction comprising unreacted alcohol and isopentane, and an intermediate boiling fraction comprising normal pentene and normal pentane, said intermediate boiling fraction having a lower concentration of isopentane than said low boiling fraction;
   (c) passing said intermediate boiling stream to a reaction zone for the skeletal isomerization of normal pentenes and contacting said intermediate boiling stream with an isomerization catalyst at isomerization conditions;
   (d) withdrawing an isomerization zone effluent stream comprising isopentene from said isomerization zone and passing said isomerization zone effluent to said etherification reaction zone.

7. The process of claim 6 wherein said alcohol comprises methanol and said product comprises a methyl tertiary amyl ether.

8. The process of claim 6 wherein said feedstream is contacted with a selective hydrogenation catalyst at selective hydrogenation conditions in a selective hydrogenation zone to selectively saturate diolefins to monoolefins.

9. The process of claim 6 wherein said distillation zone comprises a single reactive distillation column, said intermediate etherification effluent stream enters said column at a location below said catalyst bed, and said high boiling, said low boiling, and said intermediate boiling fractions are withdrawn as bottoms, overhead, and sidecut streams, respectively.

10. The process of claim 6 wherein said intermediate boiling fraction is mixed with a hydrogen rich recycle stream before entering said isomerization zone and the concentration of water, and oxygenate compounds in said intermediate boiling fraction is reduced to below 100 wppm of water equivalents before mixing said intermediate boiling stream with said hydrogen rich recycle stream.

11. A process for the production of tertiary butyl ether from a feedstream including normal butene, isobutene, normal butane, and isobutane, said process comprising:
   (a) mixing said feedstream and isomerization effluent stream with a $C_1$–$C_5$ monohydroxy alcohol to produce a combined feed and contacting said combined feed with an etherification catalyst in an etherification zone at etherification conditions to react isobutenes with said alcohol and produce an intermediate etherification effluent stream comprising tertiary butyl ether, unreacted alcohol, normal butane, normal butene, isobutane, and isobutene;
   (b) passing said intermediate etherification effluent to a reactive distillation zone containing a bed of etherification catalyst and contacting said etherification zone effluent and said alcohol in said bed of catalyst at etherification conditions, withdrawing from said distillation zone at a location below said bed of catalyst a high boiling fraction comprising said tertiary butyl ether and withdrawing from said distillation zone at a location above said bed of catalyst, a low boiling fraction comprising unreacted alcohol and said isobutane and an intermediate boiling fraction comprising normal butene and normal butane, said intermediate boiling fraction having a lower concentration of isobutane than said low boiling fraction;
   (c) passing said intermediate boiling stream to a reaction zone for the skeletal isomerization of normal butenes and contacting said intermediate boiling stream with an isomerization catalyst at isomerization conditions; and
   (d) withdrawing an isomerization zone effluent stream comprising isobutene from said isomerization zone and passing said isomerization zone effluent to said etherification reaction zone.

12. The process of claim 11 wherein said alcohol comprises methanol and said product comprises a methyl tertiary butyl ether.

13. The process of claim 11 wherein said feedstream is contacted with a selective hydrogenation catalyst at selective hydrogenation conditions in a selective hydrogenation zone to selectively saturate diolefins to monoolefins.

14. The process of claim 11 wherein said distillation zone comprises a single reactive distillation column, said intermediate etherification effluent stream enters said column at a location below said catalyst bed, and said high boiling, said low boiling, and said intermediate boiling fractions are withdrawn as bottoms, overhead, and sidecut streams, respectively.

15. The process of claim 11 wherein said intermediate boiling fraction is mixed with a hydrogen rich recycle stream before entering said isomerization zone and the concentration of water and oxygenate compounds in said intermediate boiling fraction are reduced to below 100 wppm of water equivalents before mixing said intermediate boiling with said hydrogen rich recycle stream.

16. The process of claim 1 wherein said distillation zone comprises a single distillation column and said high boiling, said low boiling, and said intermediate boiling fractions are withdrawn as bottoms, overhead, and sidecut stream, respectively.

* * * * *